(12) United States Patent
Ohba et al.

(10) Patent No.: US 8,211,074 B2
(45) Date of Patent: Jul. 3, 2012

(54) ABSORBENT ARTICLE INCLUDING UNDERGARMENT FASTENER ADHESIVE HAVING IMPROVED ADHESIVE PATTERN

(75) Inventors: Kiyoe Ohba, Fukuoka (JP); Dennis Osamu Hirotsu, Kobe Hyogo (JP)

(73) Assignee: The Procter and Gamble Company, Cincinnati, OH (US)

( * ) Notice: Subject to any disclaimer, the term of this patent is extended or adjusted under 35 U.S.C. 154(b) by 2443 days.

(21) Appl. No.: 10/360,726

(22) Filed: Feb. 7, 2003

(65) Prior Publication Data
US 2003/0163109 A1 Aug. 28, 2003

Related U.S. Application Data

(60) Provisional application No. 60/358,921, filed on Feb. 22, 2002.

(51) Int. Cl.
*A61F 13/15* (2006.01)
*A61F 13/20* (2006.01)

(52) U.S. Cl. ......... 604/385.05; 604/385.03; 604/385.02; 604/385.01

(58) Field of Classification Search ........ 604/385.02–385.03, 385.05, 385.201, 604/387, 385.13–385.14; 2/53–58
See application file for complete search history.

(56) References Cited

U.S. PATENT DOCUMENTS

| | | | | |
|---|---|---|---|---|
| 3,575,175 A | * | 4/1971 | McGuire | 604/387 |
| 3,646,937 A | * | 3/1972 | Gellert | 604/390 |
| 3,897,783 A | * | 8/1975 | Ginocchio | 604/387 |
| 3,901,237 A | * | 8/1975 | Cepuritis et al. | 604/390 |
| 3,973,567 A | * | 8/1976 | Srinivasan et al. | 604/385.05 |
| 4,321,924 A | * | 3/1982 | Ahr | 604/378 |
| 4,413,621 A | * | 11/1983 | McCracken et al. | 602/52 |
| 4,600,001 A | * | 7/1986 | Gilman | 602/52 |
| 4,605,404 A | * | 8/1986 | Sneider | 604/385.05 |

(Continued)

FOREIGN PATENT DOCUMENTS

CA 2151437 12/1995

(Continued)

OTHER PUBLICATIONS

PCT International Search Report dated Jun. 8, 2003.

*Primary Examiner* — Tatyana Zalukaeva
*Assistant Examiner* — Susan Su
(74) *Attorney, Agent, or Firm* — Andres E. Velarde; Andrew J. Hagerty; Gary J. Foose

(57) ABSTRACT

An absorbent article having a backsheet. The backsheet has a garment facing side and a first end edge in the first end region. The absorbent article has an adhesive attachment mechanism on the garment facing side of the backsheet for securing the absorbent article to an undergarment. The adhesive attachment mechanism includes a central adhesive section on or along the longitudinal centerline and a pair of side adhesive sections, each transversely outboard of the central adhesive section. Side adhesive sections have first ends in the first end region. First ends of side adhesive sections extend substantially to the first end edge of the backsheet. First end of the central adhesive section is at least about 5 mm from the first end edge of the backsheet such that an adhesive free area is formed between the first end of the central adhesive section and the first end edge of the backsheet.

14 Claims, 4 Drawing Sheets

U.S. PATENT DOCUMENTS

| | | | |
|---|---|---|---|
| 4,690,680 A | 9/1987 | Higgins | |
| 4,701,178 A | 10/1987 | Glaug et al. | |
| 5,111,934 A * | 5/1992 | Morin | 206/229 |
| 5,243,202 A | 9/1993 | Mori et al. | |
| 5,284,789 A | 2/1994 | Mori et al. | |
| H1363 H * | 10/1994 | Leeker | 206/440 |
| 5,367,179 A | 11/1994 | Mori et al. | |
| 5,413,568 A * | 5/1995 | Roach et al. | 604/358 |
| 5,429,630 A * | 7/1995 | Beal et al. | 604/385.04 |
| 5,533,962 A * | 7/1996 | Peterman et al. | 602/54 |
| 5,591,153 A * | 1/1997 | Mattingly, III | 604/387 |
| 5,824,004 A * | 10/1998 | Osborn et al. | 604/385.04 |
| 5,951,536 A * | 9/1999 | Osborn et al. | 604/387 |
| 6,821,270 B2 * | 11/2004 | Rosenfeld | 604/385.04 |
| 2002/0013566 A1 | 1/2002 | Chappell et al. | |
| 2002/0058921 A1 | 5/2002 | Sigl | |

FOREIGN PATENT DOCUMENTS

| | | | |
|---|---|---|---|
| DE | 2930929 A * | 2/1981 | |
| EP | 607986 A1 * | 7/1994 | |
| EP | 680740 A1 * | 11/1995 | |
| EP | 0 923 921 A1 | 6/1999 | |
| EP | 0 689 821 B1 | 2/2000 | |
| EP | 1181917 A2 * | 2/2002 | |
| JP | UM S49-138690 | 3/1973 | |
| JP | S49-097489 | 9/1974 | |
| JP | 62-189725 U | 12/1987 | |
| JP | 64-033502 | 2/1989 | |
| JP | UM H04-120733 | 10/1992 | |
| JP | 05-317360 | 12/1993 | |
| JP | 7-328068 | 12/1995 | |
| WO | WO 93/01783 A1 | 2/1993 | |
| WO | WO 96/10978 A1 | 4/1996 | |
| WO | WO 96/38117 A1 | 12/1996 | |
| WO | WO 9741818 A1 * | 11/1997 | |
| WO | WO 97/47266 | 12/1997 | |
| WO | WO 9820823 A2 * | 5/1998 | |
| WO | WO 00/72790 A1 | 12/2000 | |

\* cited by examiner

ABSORBENT ARTICLE INCLUDING UNDERGARMENT FASTENER ADHESIVE HAVING IMPROVED ADHESIVE PATTERN

CROSS REFERENCE TO RELATED APPLICATION

This application claims the benefit of U.S. Provisional Application No. 60/358,921, filed on Feb. 22, 2002.

FIELD OF THE INVENTION

The present invention relates to absorbent articles. More particularly, the present invention relates to an absorbent article which includes an adhesive attachment means having an improved adhesive pattern on the garment facing side of a backsheet.

BACKGROUND

Absorbent articles such as sanitary napkins, pantiliners and incontinent pads are devices that are typically worn in the crotch region of an undergarment. More specifically, sanitary napkins and pantiliners, for example, are worn by women in a pair of panties that is normally positioned between the wearer's legs, adjacent to the perineum area. Sanitary napkins and pantiliners are designed to absorb and retain body fluids or discharges (e.g., urine and menses) from the body of women and to prevent body and clothing soiling. A wide variety of shapes and dimensions of sanitary napkins and pantiliners is currently used by women for the collection of body fluids.

In order to prevent soiling, these absorbent articles must be securely maintained in close proximity to and in conformity with the body of the wearer. The maintenance of the article against the body is known as "good body contact". Good body contact enables the absorbent articles to absorb the vast majority of body fluids before they have an opportunity to flow quickly along the body contacting surface of the absorbent articles or the skin of the wearer, thereby preventing clothing and body soiling. In order to securely maintain such absorbent articles in close proximity to the body of the wearer, the absorbent articles have an adhesive attachment means on the garment facing side of the backsheet. The adhesive attachment means is used to secure the absorbent articles in the crotch region of undergarments. The adhesive attachment means usually includes a pressure sensitive adhesive disposed on the garment facing side of the backsheet.

While absorbent articles having adhesive attachment means are convenient and comfortable, these absorbent articles still have certain disadvantages in handling for use, in particular, for thin sanitary napkins and pantiliners which have a thickness less than about 3 mm, for example. Specifically, pantiliners typically have a removable release liner which covers and protects the adhesive attachment means before use of pantiliners. Such a removable release liner is typically a sheet member and has a perimeter which is coincident with that of the backsheet of the pantiliner. Since the adhesive attachment means normally extends longitudinally to the end edge of the pantiliner (i.e., the end edge of the backsheet), it is not easy for users to initiate a removal of the removable release liner from the pantiliner by separating it from the adhesive attachment means at the end edge portion of pantiliner.

Thus, there is a need for an absorbent article that can be handled more easily for a removal of removable release liner.

SUMMARY

In one aspect, the present invention is directed to an absorbent article designed to be worn in the crotch region of an undergarment. The absorbent article has a longitudinal center line, a first end region, a second end region, and a central region disposed between the first and second regions. The absorbent article comprises an absorbent core and a backsheet associated with the absorbent core. The backsheet has a garment facing side and a first end edge in the first end region. The absorbent article further comprises adhesive attachment means disposed on the garment facing side of the backsheet for securing the absorbent article to an undergarment. The adhesive attachment means has an adhesive pattern which includes (a) a central adhesive section disposed on or along the longitudinal center line. The central adhesive section has a first end in the first end region. The adhesive pattern further includes (b) a pair of side adhesive sections each disposed transversely outboard of the central adhesive section, respectively. Each of the side adhesive section has a first end in the first end region. The first ends of each side adhesive section extends substantially to the first end edge of the backsheet. The first end of the central adhesive section is at least about 5 mm away from the first end edge of the backsheet such that an adhesive free area is formed between the first end of the central adhesive section and the first end edge of the backsheet.

In another aspect of the invention, an absorbent article comprising an absorbent core and a backsheet associated with the absorbent core. The backsheet has a garment facing side and a first end edge in the first end region. The absorbent article further comprises adhesive attachment means disposed on the garment facing side of the backsheet for securing the absorbent article to an undergarment. The adhesive attachment means has an adhesive pattern which includes an adhesive section and an adhesive free area. The absorbent article further comprises a removable release liner which covers the adhesive pattern. The removable release liner has a notch which is positioned such that the adhesive free area of the adhesive pattern is exposed.

The foregoing answers the need for an absorbent article that can be handled more easily for a removal of removable release liner.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION

Figure 1:
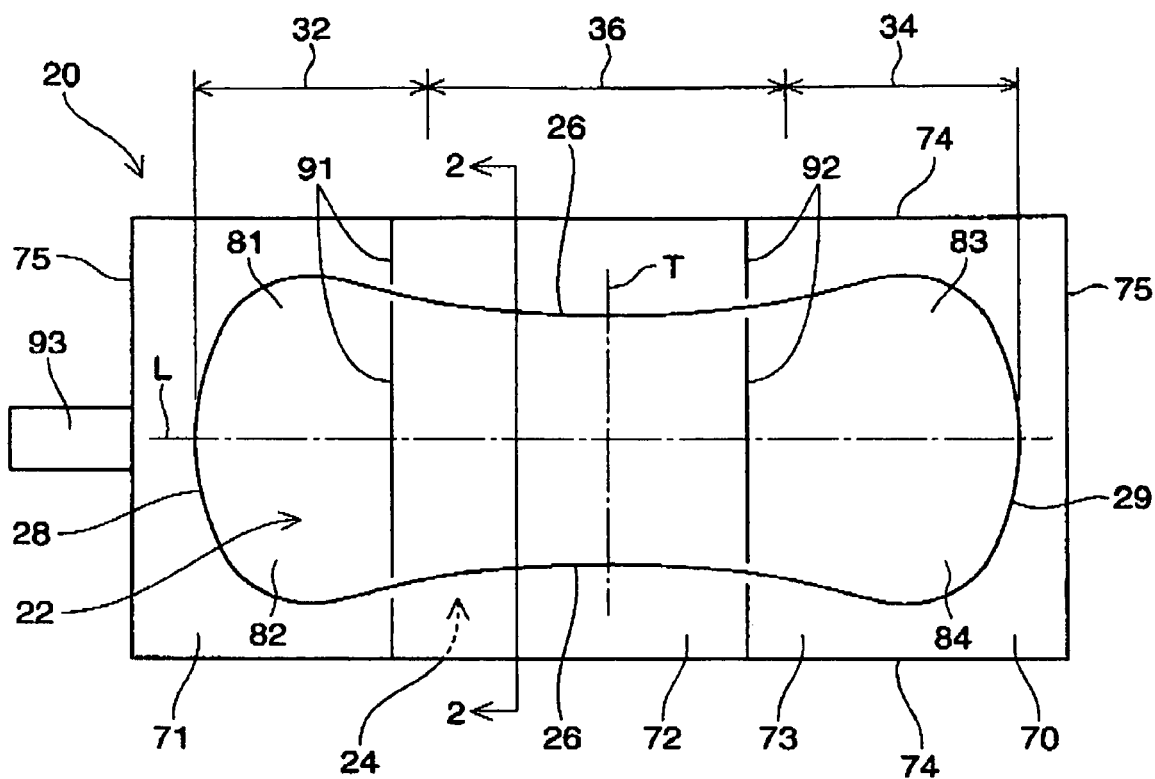
FIG. 1 is a top plan view of a pantiliner which is one preferred embodiment of the present invention.

All cited references are incorporated herein by reference in their entireties. Citation of any reference is not an admission regarding any determination as to its availability as prior art to the claimed invention.

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges, such as body fluids. More specifically, the term refers to articles which are placed against or in proximity to the body of the wearer to absorb and contain the various exudates discharged from the body. Herein, "absorbent article" is intended to include sanitary napkins, pantiliners, diapers, and incontinence pads (and other articles worn in the crotch region of a garment). The present invention is preferably applied to pantiliners, sanitary napkins or incontinent pads.

Herein, "disposable" refers to articles which are intended to be discarded after a single use and preferably recycled, composted, or otherwise disposed of in an environmentally compatible manner. (That is, they are not intended to be laundered or otherwise restored or reused as an absorbent article.) Herein, "pantiliner" and "sanitary napkin" refer to articles which are worn by females adjacent to the pudendal region which are intended to absorb and contain the various exudates which are discharged from the body (e.g., blood, menses, and urine). Compared with sanitary napkins, pantiliners generally have smaller length, width and thickness, and have a smaller absorbent capacity. Although the present invention is shown in the drawings as a pantiliner napkin that is intended to replace conventional pantiliners, it should be understood that the present invention is not limited to the particular types or configurations of absorbent articles shown in the drawings.

Herein, "body facing side" refers to sides of absorbent articles and/or their component members which face the body of the wearer, while the term "garment facing side" refers to the opposite sides of the absorbent articles and/or their component members that face away from the wearer when the absorbent articles are worn. Absorbent articles and their component members thereof, including the topsheet, backsheet, absorbent core, and any individual layers of their component members, have a body facing side and a garment facing side.

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

FIG. 1 is a top plan view of a disposable absorbent article (i.e., a pantiliner 20) which is one preferred embodiment of the present invention. Referring to FIG. 1, the pantiliner 20 has a body facing side 22, a garment facing side 24 opposed to the body facing side 22, first and second end regions 32, 34, a central region 36 disposed between the first and second end regions 32, 34, longitudinal side edges 26, and first and second end edges 28 and 29. The pantiliner 20 shown in FIG. 1 is viewed from the body facing side 22. The pantiliner 20 shown in FIG. 1 has a generally hourglass shape, i.e., the longitudinal side edges 26 are curvilinear wherein the pantiliner 20 is narrower in the transverse direction in the central region 36 than the first and second end regions 32 and 34. In the embodiment shown in FIG. 1, the pantiliner 20 has four side lobes 81-84. The pantiliner 20 further includes a wrapper sheet 70 which forms an individual package when it is folded.

The pantiliner 20 has two centerlines, i.e., a longitudinal centerline L and a transverse centerline T. Herein, "longitudinal" refers to a line, axis or direction in the plane of the pantiliner 20 that is generally aligned with (e.g., approximately parallel to) a vertical plane which bisects a standing wearer into left and right body halves when the pantiliner 20 is worn. Herein, "transverse" or "lateral", are interchangeable, and refer to a line, axis or direction which lies within the plane of the pantiliner 20 that is generally perpendicular to the longitudinal direction.

Figure 2:
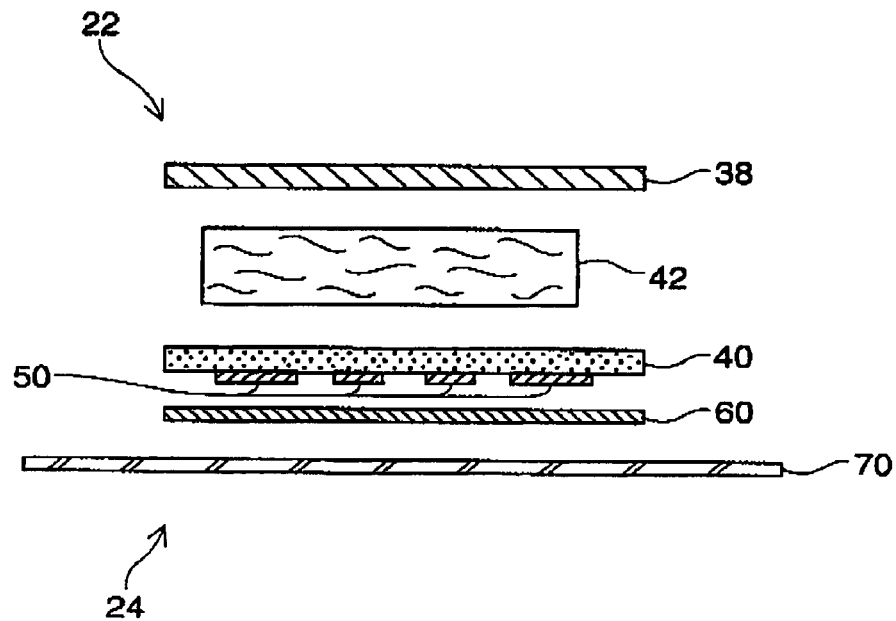
FIG. 2 is a cross-sectional view of the pantiliner shown in FIG. 1, taken along the line 2-2.

FIG. 2 is a cross-sectional view of the pantiliner 20 shown in FIG. 1, taken along the line 2-2. The pantiliner 20 includes a liquid pervious topsheet 38, a liquid impervious backsheet 40, an absorbent core 42 disposed between the topsheet 38 and the backsheet 40, an adhesive attachment means 50 disposed on the garment facing side 24 of the backsheet 40, a removable release liner 60 for covering and protecting the adhesive attachment means 50, and the wrapper sheet 70. The adhesive attachment means 50 of the pantiliner 20 is used for attaching the pantiliner 20 to the wearer's undergarment. More specifically, the adhesive attachment means 50 is adapted to secure the pantiliner 20 to the crotch region of the wearer's undergarment.

Figure 3:
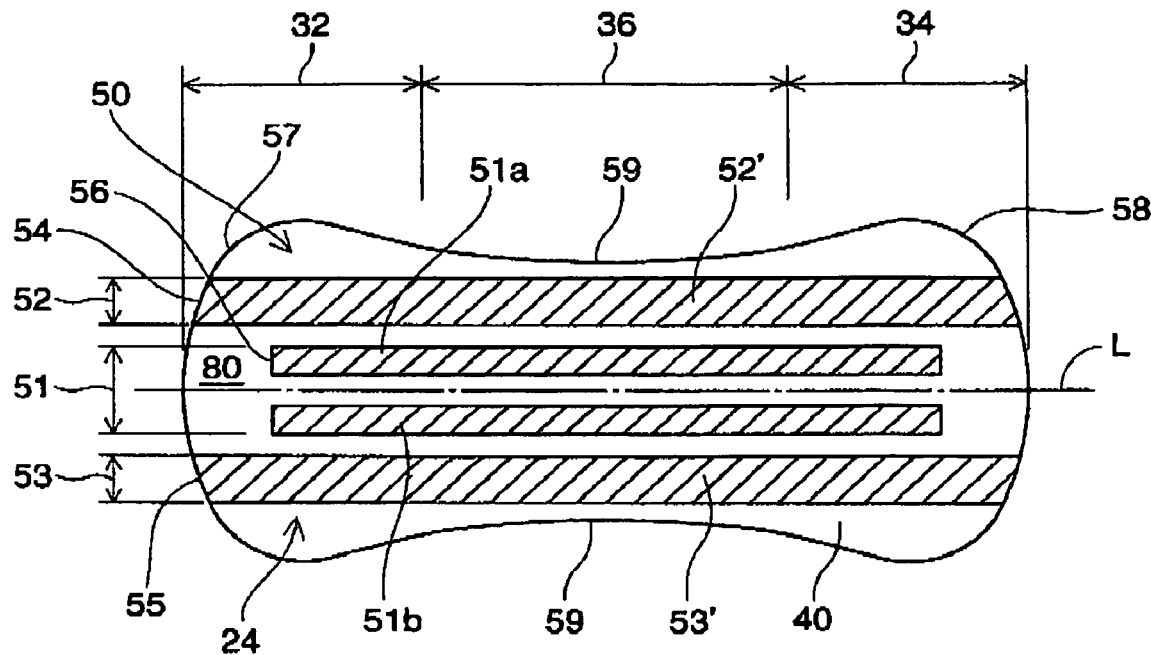
FIG. 3 is a plan view of the garment facing side of the backsheet shown in FIG. 2.

FIG. 3 is a plan view of the garment facing side 24 of the backsheet 40 shown in FIG. 2. This figure particularly shows one preferred example of the adhesive attachment means 50. Referring to FIG. 3, the backsheet 40 has a perimeter which includes a first end edge 57 (which forms the first end edge 28 of the pantiliner 20 shown in FIG. 1) in the first end region 32, a second end edge 58 in the second end region 34, and side edges 59 (which also form the longitudinal side edges 26 of the pantiliner 20 shown in FIG. 1). The adhesive attachment means 50 is disposed on the garment facing side 24 of the backsheet 40. The adhesive attachment means 50 has an adhesive pattern which includes a central adhesive section 51 disposed on or along the longitudinal center line L. The central adhesive section 51 has a first end 56 in the first end region 32. The adhesive pattern further includes a pair of side adhesive sections 52 and 53 each disposed transversely outboard of the central adhesive section 51, respectively. The side adhesive sections 52 and 53 have first ends 54 and 55 in the first end region, respectively. The first ends 54 and 55 of the side adhesive sections 52 and 53 extend substantially to the first end edge 57 of the backsheet 24. Herein, "extend substantially to an end edge" refers to one element extends to reach a region which is within 3 mm from the end edge of another element. In other words, the first ends 54 and 55 of the side adhesive sections 52 and 53 are coincident with the first end edge 57 of the backsheet 24 within a range of 3 mm. Herein, "coincident with" or "coincide with" refers to the edges of two members that meet to form a common edge at at least one corresponding section in each member.

In preferred embodiments, the first end 56 of the central adhesive section 51 is at least about 5 mm away from the first end edge 57 of the backsheet 40 such that an adhesive free area 80 is formed between the first end 56 of the central adhesive section 51 and the first end edge 57 of the backsheet 40. Preferably, the first end 56 of the central adhesive section 51 is from about 10 mm to about 50 mm, more preferably from about 15 mm to about 25 mm away from the first end edge 57 of the backsheet 40.

Preferably, the adhesive free area 80 of the adhesive pattern has an enough area for the tip of user's one finger so that users can take the adhesive free area 80 of the pantiliner 20 with two fingers (i.e., one finger from the garment facing side 24 and another finger from the body facing side 22). This prevents users from touching the adhesive attachment means 50 when the pantiliner 20 is picked up for use. Preferred area of the adhesive free area 80 is from about 50 $mm^2$ to about 2,000 $mm^2$, more preferably from about 350 $mm^2$ to about 1,000 $mm^2$.

By providing an adhesive free area 80 which has an enough area for the tip of one finger, the pantiliner 20 can be handled more easily for a removal of the removable release liner 60, compared with conventional absorbent articles.

Figure 7:
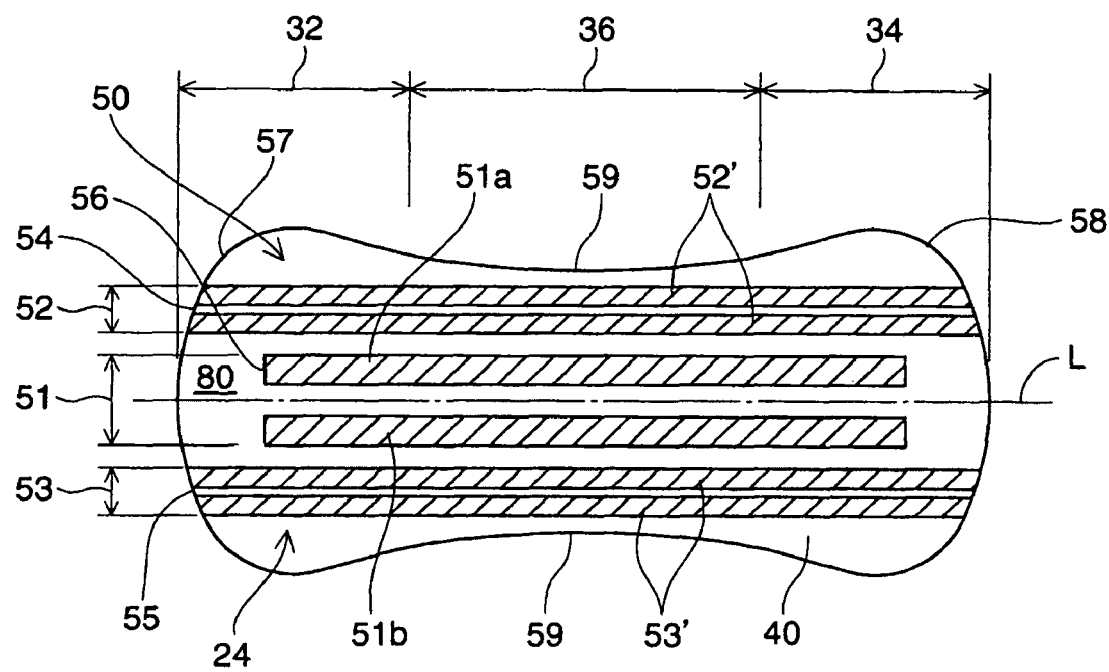
FIG. 7 is a plan view of the garment facing side of the backsheet on which each of the side adhesive sections includes a plurality of side adhesive stripes.

The central adhesive section 51 can include a single adhesive stripe (not shown in Figs.) which is disposed on or along the longitudinal center line L. Preferably, the central adhesive section 51 includes a plurality of central adhesive stripes which are disposed on or along the longitudinal center line L. In a preferred embodiment, the central adhesive section 51 includes two central adhesive stripes 51a and 51b as shown in FIG. 3. Preferably, each of the side adhesive sections 52 and 53 includes a single adhesive stripe 52' and 53' which is disposed in parallel to the longitudinal center line L, as shown in FIG. 3. Alternatively, each of the side adhesive sections 52 and 53 can include a plurality of (e.g., 2 or 3) side adhesive stripes which are disposed in parallel to the longitudinal center line L, as shown in FIG. 7.

The central adhesive section 51 and the side adhesive sections 52 and 53 preferably have straight side edges which are formed in the longitudinal direction as shown in FIG. 3. However, the central adhesive section 51 and the side adhesive sections 52 and 53 may have a non-straight (i.e., curved) portion in the longitudinal side edges if desired.

Similarly, the adhesive strips (e.g., 51a, 51b, 52' and 53') in the central adhesive section 51 and the side adhesive sections 52 and 53 preferably have straight side edges which are formed in the longitudinal direction as shown in FIG. 3. However, these adhesive strips may have a non-straight (i.e., curved) portion in the longitudinal side edges if desired.

Although the above description refers to the adhesive patterns with respect to only the first end region 32, similar adhesive patterns are preferably disposed in the second end region 34 as shown in FIG. 3. However, a different adhesive pattern from the first end region 32 may be disposed in the second end region 34 if desired.

In one preferred embodiment shown in FIG. 1, the pantiliner 20 has a longitudinal length of about 151 mm, and a traversal length (at the side lobes 81 and 82) of about 67 mm. In this design, each adhesive stripe 51a and 51b in the central adhesive section 51 has a width of about 3 mm, and each adhesive stripe 52' and 53' in the side adhesive sections 52 and 53 has a width of about 9 mm. The distance between the two stripes 51a and 51b in the central adhesive section 51 is about 6 mm. The distance between the central adhesive section 51 and each of the side adhesive sections 52 and 53 is about 4.5 mm. The distance between the first end 56 of the central adhesive section 51 and the first end edge 57 of the backsheet 40 is about 15 mm.

The adhesive attachment means 50 can be formed by any adhesive or glue known in the art for securing absorbent articles in the crotch region of undergarments. A particularly preferred adhesive is a pressure-sensitive adhesive. Suitable pressure-sensitive adhesives are described in greater detail in U.S. Pat. No. 4,917,697 issued to Osborn, III, et al. on Apr. 17, 1990. In one preferred embodiment, the adhesive attachment means 50 is formed by a pressure-sensitive adhesive which is available from National Starch Corporation, Italy, under Code No. 834-2823. In one preferred embodiment, the adhesive stripes 51a, 51b, 52' and 53' have a basis weight of about 35.5 $g/m^2$ of the pressure-sensitive adhesive. The adhesive attachment means 50 can be formed on the backsheet 40 (or a backsheet material) by any adhesive or glue application manner known in the art.

Figure 4:
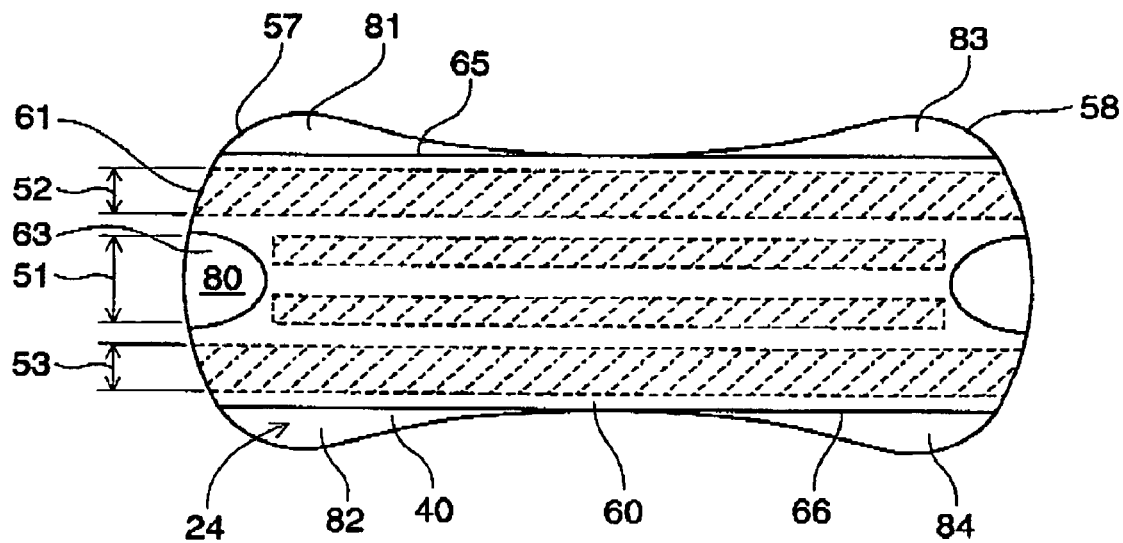
FIG. 4 is a plan view of the garment facing side of the backsheet which is covered by a removable release liner.

FIG. 4 is a plan view of the garment facing side 24 of the backsheet 40 which is covered by the removable release liner 60. The removable release liner 60 covers at least a part of, preferably the entire portion of the adhesive pattern (i.e., the central adhesive section 51 and the side adhesive sections 52 and 53) as shown in FIG. 4. The removable release liner 60 has a first end edge 61 which has a portion that is coincident, at least partially, with the first end edge 57 of the backsheet 40 as shown in FIG. 4. The removable release liner 60 preferably has a notch 63 which is positioned such that at least a part of, more preferably 50% of, more preferably 70% of the adhesive free area 80 of the adhesive pattern on the backsheet 40 is exposed though the notch 63 as shown in FIG. 4.

The notch 63 can have any shape as long as at least a part of the adhesive free area 80 of the adhesive pattern is exposed. Preferred shapes for the notch 63 include a part of circle, oval, triangle or rectangle. The shape of the notch 63 shown in FIG. 4 is a part of oval.

The notch 63 preferably has an enough area for the tip of one finger so that users can take the adhesive free area 80 of the pantiliner 20 through the notch 63 with two fingers. This design enables users to easily initiate a removal of the removable release liner 60 from the pantiliner 20 when the pantiliner 20 is picked up for use since users can easily separate the removable release liner 60 from the adhesive attachment means 50. Preferred area of the notch 63 is from about 25 $mm^2$ to about 2,000 $mm^2$, more preferably from about 150 $mm^2$ to about 500 $mm^2$.

In a preferred embodiment, the garment facing side 24 of the removable release liner 60 has a usage description of the pantiliner 20. Such a usage description can contain any information which is useful for users. One example of usage description is "Please remove this release liner before use.". The usage description is preferably made by printing on the garment facing side 24 of the removable release liner 60. Any printing method known in the art can be used.

Figure 6:
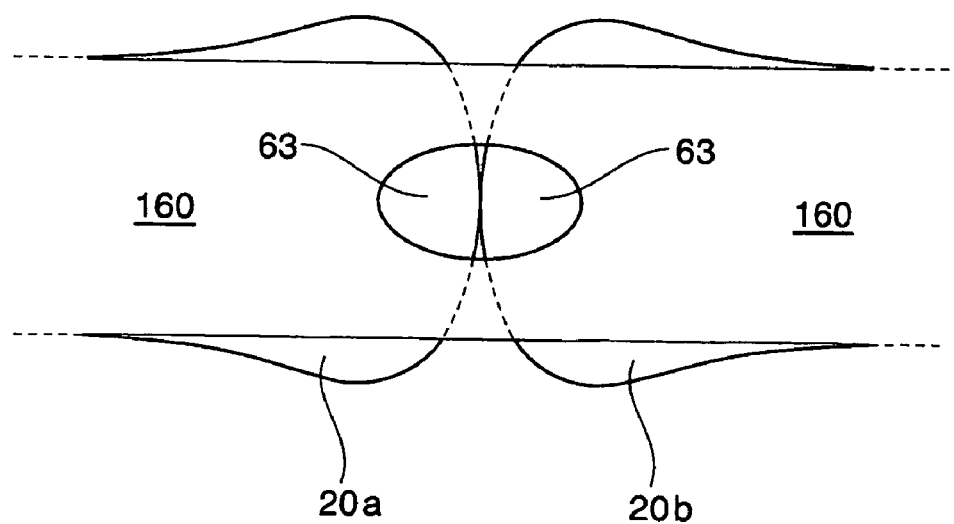
FIG. 6 is a plan view of a part of process, as one preferred embodiment, for applying a removable release liner member to two succeeding pantiliners which are manufactured in the machine direction.

FIG. 6 shows a part of process, as one preferred embodiment, for applying a removable release liner member 160 to two succeeding pantiliners 20a and 20b which are manufactured in the machine direction MD. In this embodiment, the shape for two notches 63 is a part of oval. The two notches 63 can be formed in the removable release liner member 160 by one cutting operation.

As shown in FIG. 1, the pantiliner 20 includes the wrapper sheet 70. Preferably, the wrapper sheet 70 is joined to the garment facing side 24 of the removable release liner 60 by an adhesive means. Such an adhesive means can be disposed on any portion or location of the garment facing side 24 of the removable release liner 60. Preferably, the adhesive means is provided on the whole area of the garment facing side 24 of the removable release liner 60.

Preferably, the bonding strength between the removable release liner 60 and the wrapper sheet 70 is greater than the bonding strength between the removable release liner 60 and the adhesive attachment means 50. Specifically, the bonding strength between the removable release liner 60 and the wrapper sheet 70 is preferably at least 10 gf, preferably from about 500 gf to about 600 gf.

When the pantiliner 20 is picked up by users, the removable release liner 60 is left on the body facing side 22 of the wrapper sheet 70 since the removable release liner 60 and the wrapper sheet 70 are joined. Thus, users can handle the two sheets (i.e., the removable release liner 60 and the wrapper sheet 70) together for disposal.

In an alternative preferred embodiment, the pantiliner 20 does not include a removable release liner. Instead, a wrapper sheet which has a removable release treatment on the body facing side 22 is used for covering and protecting the adhesive pattern (i.e., the central adhesive section 51 and the side adhesive sections 52 and 53). Such a removable release treatment can be provided by treating the body facing side 22 of the wrapper sheet 70 with a silicone compound which is known as a silicone coating or a release coating in the art. The wrapper sheet 70 can be zone coated (i.e., partially coated) with the release coating only in the areas of the adhesive attachment means 50, or can be entirely release coated throughout the body facing side 22 if desired.

In the embodiment shown in FIG. 4, the pantiliner 20 generally has an hourglass shape having four side lobes 81-84, and the removable release liner 60 has straight side edges 65 and 66. In this embodiment, the side lobes 81-84 of the pantiliner 20 extend beyond the straight side edges 65 and 66 of the removable release liner 60 in the first and second regions 32 and 34. The embodiment shown in FIG. 4 is preferred since the removable release liner 60 is not seen by the user when the pantiliner 20 is viewed from the body facing side 22.

The removable release liner 60 can be formed by any sheet or film material known in the art. Preferably, the removable release liner 60 has a removable release treatment on the body facing side 22. Such a removable release treatment can be provided by treating the body facing side 22 of the removable release liner 60 with a silicone compound which is known as a silicone coating or a release coating in the art. The removable release liner 60 is preferably entirely release coated throughout the body facing side 22. A preferred material for the removable release liner 60 is a paper material which is available from Akrosil Corporation, Holland, under Code No. BL40GMGA Silox D3 H/O.

As shown in FIG. 1, the wrapper sheet 70 has a perimeter defined by longitudinal side edges 74 and end edges 75. The longitudinal side edges 74 of the wrapper sheet 70 extend transversely outward beyond the respective longitudinal side edges 26 of the pantiliner 20. The end edges 75 of the wrapper sheet 70 extend longitudinally outward beyond the respective end edges 28 and 29 of the pantiliner 20. This arrangement provides a wrapper sheet having sufficient longitudinal and traversal extent to conceal and to protect the pantiliner 20 in the later described folded configurations.

The wrapper sheet 70 may be made of films, kraft papers, calendered papers, or other materials known in the art. Preferably, the wrapper sheet 70 is a flexible polyethylene film. A preferred polyethylene film is available from Boehme Corporation, Germany, under Code No. Pouch-P1.

The pantiliner 20, together with the removable release liner 60 and the wrapper sheet 70, is preferably folded about two spaced-apart laterally oriented fold lines 91 and 92 to form trisections 71-73 as shown in FIG. 1. Herein, "spaced-apart laterally oriented fold lines" refers to longitudinally offset lines, generally parallel in the lateral direction, and about which the pantiliner 20 including the removable release liner 60 and the wrapper sheet 70 is commonly folded. After the pantiliner 20 is folded, the longitudinal side edges 74 of the wrapper sheet 70 are sealed by an application of heat and pressure as known in the art. (The sealed side edge portions 74 of the wrapper sheet 70 are indicated by the reference numbers 98 in FIG. 5.) Then, the end edge 75 of the wrapper sheet 70 is affixed to the other end portion of the wrapper sheet 70 by an adhesive tape 93 thereby producing an individually packaged product which contains the pantiliner 20.

Figure 5:
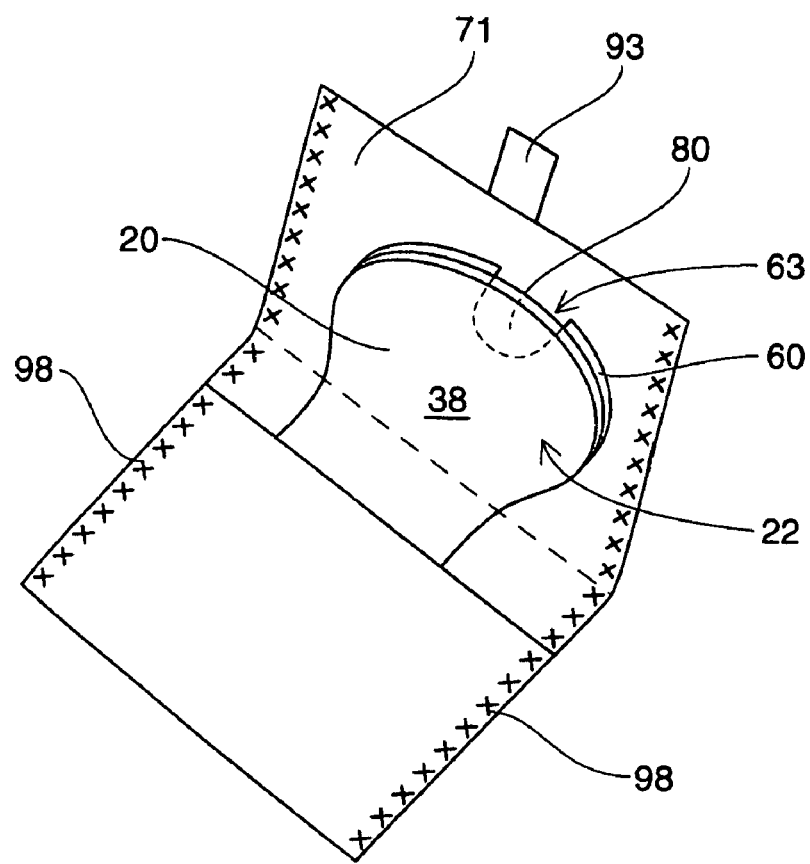
FIG. 5 is a perspective view of an individually packaged product which contains the pantiliner shown in FIG. 1.

FIG. 5 is a perspective view of such an individually packaged product. In this figure, the adhesive tape 93 and the sealed section 71 have been released to open the package. A part of the pantiliner 20 which has the adhesive free area 80 is seen from the body facing side 22 of the topsheet 38. The removable release liner 60 which has the notch 63 is also seen in this figure. In this embodiment, the removable release liner 60 is joined to the wrapper sheet 70 (not shown in FIG. 5). Users can pick up the pantiliner 20 by taking the portion of the adhesive free area 80 with the tips of the two fingers. After the pantiliner 20 is picked up, the removable release liner 60 and the wrapper sheet 70 are left since they are joined. Thus, users can handle these two sheet materials for disposal at once (i.e., users do not need to take care of these two sheet materials separately).

The absorbent core 42 is capable of receiving, absorbing or retaining body fluids discharged (e.g., menses, vaginal discharge, urine, and other body exudates). The absorbent core 42 is preferably compressible, conformable, and non-irritating to the wearer's skin. The absorbent core 42 may be manufactured in a wide variety of sizes and shapes (e.g., rectangular, oval, hourglass, "T" shaped, dog bone, asymmetric, etc.). The absorbent core 42 can be formed by a single layer material or a plurality of layered materials. The absorbent core 42 may include any of a wide variety of liquid-absorbent materials commonly used in absorbent articles, such as comminuted wood pulp, which is generally referred to as airfelt. Examples of other suitable absorbent materials for use in the absorbent core include tissue materials including tissue wraps and tissue laminates; creped cellulose wadding; meltblown polymers including coform; chemically stiffened, modified or cross-linked cellulosic fibers; synthetic fibers such as crimped polyester fibers; peat moss; absorbent foams; absorbent sponges; absorbent gelling materials (in the particulate form or the fibrous form); or any equivalent material or combinations of materials, or mixtures of these. Herein, "chemically stiffened fibers" means any fibers which have been stiffened by chemical means to increase stiffness of the fibers under both dry and wet conditions.

In one preferred embodiment, the absorbent core 42 is one ply of an air laid tissue material which is available from Concert GmbH, Falkenhagen, Germany under Code No. GH150. In another preferred embodiment, the absorbent core 42 is an air laid tissue material which is available from Buckeye Cellulose Corporation, Tenn., USA under Code No. Foley NMC. In an yet another preferred embodiment, the absorbent core 42 includes a fibrous absorbent gelling material. A preferred fibrous absorbent gelling material is available from Concert Corporation, Germany, under Code No. GH100.1008.

In a preferred embodiment, an acquisition layer or a secondary topsheet (not shown in Figs.) is additionally disposed between the topsheet 38 and the absorbent core 42. The acquisition layer quickly transports discharged body fluids received by the topsheet 38 to other parts of the acquisition layer and the absorbent core 42, although it may temporarily hold such fluids until they can be absorbed by the absorbent core 42. The distribution function of the acquisition layer is of particular importance in order to more fully utilize the capacity of the absorbent core 42. Thus, while the acquisition layer may comprise a wide variety of absorbent materials, it preferably comprises a fibrous material that can rapidly transport fluid and not collapse upon being wetted so that the acquisition layer can effectively acquire and distribute second and successive fluids.

The acquisition layer can be made from any materials which have fluid transportation functions known in the art. The acquisition layer may, for example, be comprised of woven, nonwoven or tissue materials. The fibers or other components of these materials may be synthetic or natural, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers. The acquisition layer may also be at least partially comprised of cross-linked cellulose fibers. The acquisition layer, if it is a nonwoven, can be made by a number of different processes. These include, but are not limited to: air laid, wet laid, melt-blown, spunbonded, carded, thermally bonded, air-through bonded, powder bonded, latex bonded, solvent bonded, spunlaced, and a combination.

The backsheet 40 is impervious to body fluids and is preferably manufactured from a thin plastic film, although other flexible liquid impervious materials may also be used. Herein, "flexible" refers to materials which are compliant and will readily conform to the general shape and contours of the human body. The backsheet 40 prevents the body fluids absorbed and contained in the absorbent core 42 from wetting articles which contact the absorbent article such as bedsheets, pants, pajamas and undergarments. The backsheet 40 may thus include a woven or nonwoven material, polymeric films such as thermoplastic films of polyethylene or polypropylene, or composite materials such as a film-coated nonwoven material. A suitable backsheet material is a polyethylene film having a thickness of from about 0.012 mm (0.5 mil) to about 0.051 mm (2.0 mils). The backsheet 40 may be embossed and/or matte finished to provide a more clothlike appearance. Further, the backsheet 40 may permit vapors to escape from the absorbent core 42 (i.e., the backsheet is breathable) while still preventing body fluids from passing through the backsheet. A preferred microporous polyethylene film which is available from Tredegar Corporation, Virginia, USA, under Code No. XBF-112W.

In one preferred embodiment, the breathable backsheet material is a laminate of an apertured film such as that described in U.S. Pat. No. 3,929,135issued to Thompson which is inverted so that the smaller openings of the tapered capillaries face the absorbent core 42 which is adhesively laminated to a microporous film such as that described in U.S. Pat. No. 4,777,073 issued to Sheth on Oct. 11, 1988.

The absorbent article of the present invention can generally have any thickness including relatively thick, intermediate thickness, relatively thin, or even very thin (or "ultra thin"). An example of "ultra-thin" sanitary napkin is described in U.S. Pat. Nos. 4,950,264 and 5,009,653 issued to Osborn preferably has a caliper of less than about 3 mm. The absorbent article is preferably relatively flexible, so that is comfortable for the wearer.

The topsheet 38 is preferably compliant, soft feeling, and non-irritating to the wearer's skin. Further, the topsheet 38 is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable topsheet for use in the sanitary napkins disclosed includes an apertured formed film. Apertured formed films are preferred for the topsheet 38 because they are pervious to body exudates and, if properly apertured, have a reduced tendency to allow liquids to pass back through and rewet the wearer's skin. Thus, the body facing side 22 of the formed film (i.e., the body facing side 22 of the sanitary napkin) remains dry, thereby reducing body soiling and creating a more comfortable feel for the wearer.

Preferably, the body facing side 22 of the pantiliner 20 is hydrophilic so that liquids will be transferred through the topsheet 38 more readily. If the topsheet 22 is made of a hydrophobic material, at least the upper side (i.e., the body facing side 22) of the topsheet 38 is treated to be hydrophilic so that liquids will transfer through the topsheet 38 more rapidly. This diminishes the likelihood that menstrual fluid will flow off the topsheet rather than flowing into and being absorbed by the absorbent core 42. The body facing side of the topsheet 38 can be made hydrophilic by treating it with a surfactant. A preferred topsheet material is an apertured polyethylene film which is available from BP Chemical Corporation, Germany, under Code No. 45105.

In one preferred embodiment, a hybrid topsheet is used as the topsheet 38. The hybrid topsheet includes a fibrous layer (e.g., a nonwoven layer) disposed on each longitudinal sides of a film layer. Such hybrid topsheet structures are disclosed in U.S. Pat. No. 6,117,523 issued to Sugahara on Sep. 12, 2000.

The absorbent core 42 is preferably joined with the topsheet 38, the backsheet 40, or both in any manner as is known by attachment means such as those well known in the art. The backsheet 40 and/or the topsheet 38 may be joined to the absorbent core 42 or to each other by a uniform continuous layer of adhesive, a patterned layer of adhesive, or an array of separate lines, spirals, or spots of adhesive.

The portions of the topsheet 38 and backsheet 40 that extend beyond the edges of the absorbent core 42 are preferably also joined to each other. Preferably, these portions of the topsheet 38 and backsheet 40 are joined using adhesives over substantially the entire portions that extend beyond the edges of the absorbent core 42 and a crimp seal at the end edges of the pantiliner 20 where the topsheet 38 and backsheet 40 are densified by an application of pressure or heat and pressure.

In a sanitary napkin embodiment, the sanitary napkin may include an optional pair of flaps or wings (not shown in Figs.) extended outward from the central region 36, for example, of the sanitary napkin. The flaps can be in any suitable configuration known in the art. Preferred flap configurations for absorbent articles are described in U.S. Pat. Nos. 4,589,876 issued to Van Tilburg on May 20, 1986; U.S. Pat. No. 4,687,478 issued to Van Tilburg on Aug. 18, 1987; and U.S. Pat. No. 5,800,654 issued to Davis et al. on Sep. 1, 1998.

It is understood that the examples and embodiments described herein are for illustrative purpose only and that various modifications or changes will be suggested to one skilled in the art without departing from the scope of the present invention.

What is claimed is:

1. An absorbent article designed to be worn in the crotch region of an undergarment, the absorbent article having a longitudinal center line, a first end region, a second end region, and a central region disposed between the first and second regions, the absorbent article comprising:
  an absorbent core;
  a backsheet associated with the absorbent core, the backsheet having a garment facing side and a first end edge in the first end region; and
  adhesive attachment means disposed on the garment facing side of the backsheet for securing the absorbent article to an undergarment;
  the adhesive attachment means having an adhesive pattern which includes
    (a) a central adhesive section disposed on or along the longitudinal center line, the central adhesive section having a first end in the first end region, and
    (b) a pair of side adhesive sections each disposed transversely outboard of the central adhesive section, respectively, each of the side adhesive section having a first end in the first end region, the first ends of each side adhesive section extending substantially to the first end edge of the backsheet,
  wherein the first end of the central adhesive section is at least about 15 mm away from the first end edge of the backsheet such that an adhesive free area is formed between the first end of the central adhesive section and the first end edge of the backsheet;
  said absorbent article further comprising a removable release liner which covers the adhesive pattern, wherein the removable release liner has a periphery edge which has a portion that is coincident, at least partially, with the first end edge of the backsheet, wherein the removable release liner has a notch which is positioned such that at least a part of the adhesive free area of the adhesive pattern is exposed.

2. The absorbent article of the claim 1, wherein the central adhesive section includes a plurality of central adhesive stripes.

3. The absorbent article of the claim 1, wherein each of the side adhesive section includes a plurality of side adhesive stripes.

4. The absorbent article of the claim 1, further comprising a first wrapper sheet which is joined to the removable release liner.

5. The absorbent article of the claim 1, wherein the removable release liner has straight side edges, and the absorbent article has side lobes in the first or second end region which extend beyond the straight side edges of the removable release liner.

6. The absorbent article of the claim 1, wherein the notch has a shape which is a part of circle, oval, triangle or rectangle.

7. The absorbent article of the claim 1, wherein the absorbent article is a pantiliner, a sanitary napkin or an incontinent pad.

8. An absorbent article designed to be worn in the crotch region of an undergarment, the absorbent article having a longitudinal center line, a first end region, a second end region, and a central region disposed between the first and second regions, the absorbent article comprising:
  an absorbent core;
  a backsheet associated with the absorbent core, the backsheet having a garment facing side and a first end edge in the first end region; and
  adhesive attachment means disposed on the garment facing side of the backsheet for securing the absorbent article to an undergarment, the adhesive attachment means having an adhesive pattern which includes an adhesive section and an adhesive free area; and
  a removable release liner which covers the adhesive pattern, and wherein the removable release liner has a notch which is positioned such that the adhesive free area of the adhesive pattern is exposed.

9. The absorbent article of the claim 8, further comprising a first wrapper sheet which is joined to the removable release liner.

10. The absorbent article of claim 8, wherein said adhesive section includes a plurality of adhesive stripes.

11. The absorbent article of claim 8, wherein said removable release liner has a periphery edge which has a portion that is coincident, at least partially, with the first end edge of the backsheet.

12. The absorbent article of claim 8, wherein the removable release liner has straight side edges, and the absorbent article has side lobes in the first or second end region which extend beyond the straight side edges of the removable release liner.

13. The absorbent article of claim 8, wherein the notch has a shape which is a part of circle, oval, triangle or rectangle.

14. The absorbent article of claim 8, wherein the absorbent article is a pantiliner, a sanitary napkin or an incontinent pad.

* * * * *